US011006654B2

(12) United States Patent
McNeff et al.

(10) Patent No.: US 11,006,654 B2
(45) Date of Patent: May 18, 2021

(54) SAPONIN AND BACTERIAL COMPOSITIONS AND METHODS

(71) Applicant: SarTec Corporation, Anoka, MN (US)

(72) Inventors: Larry C. McNeff, Anoka, MN (US); Clayton V. McNeff, Andover, MN (US); Don Taylor, Jr., Manhattan, KS (US); Peter G. Greuel, Anoka, MN (US)

(73) Assignee: SarTec Corporation, Anoka, MN (US)

( * ) Notice: Subject to any disclaimer, the term of this patent is extended or adjusted under 35 U.S.C. 154(b) by 97 days.

(21) Appl. No.: 16/039,410

(22) Filed: Jul. 19, 2018

(65) Prior Publication Data

US 2019/0021366 A1 Jan. 24, 2019

Related U.S. Application Data

(60) Provisional application No. 62/535,407, filed on Jul. 21, 2017.

(51) Int. Cl.

| | |
|---|---|
| A23K 10/30 | (2016.01) |
| A61K 36/185 | (2006.01) |
| A61K 36/13 | (2006.01) |
| A23K 10/18 | (2016.01) |
| A61K 35/747 | (2015.01) |
| A23K 50/10 | (2016.01) |
| A61K 36/88 | (2006.01) |
| A61K 35/745 | (2015.01) |
| A61K 36/886 | (2006.01) |
| A61K 36/8965 | (2006.01) |
| A23K 20/121 | (2016.01) |
| A61K 35/741 | (2015.01) |
| A61K 36/898 | (2006.01) |
| A61K 36/77 | (2006.01) |
| A61K 36/752 | (2006.01) |
| A61K 36/48 | (2006.01) |
| A61K 35/00 | (2006.01) |

(52) U.S. Cl.
CPC .............. *A23K 10/30* (2016.05); *A23K 10/18* (2016.05); *A23K 20/121* (2016.05); *A23K 50/10* (2016.05); *A61K 35/741* (2013.01); *A61K 35/745* (2013.01); *A61K 35/747* (2013.01); *A61K 36/13* (2013.01); *A61K 36/185* (2013.01); *A61K 36/48* (2013.01); *A61K 36/752* (2013.01); *A61K 36/77* (2013.01); *A61K 36/88* (2013.01); *A61K 36/886* (2013.01); *A61K 36/898* (2013.01); *A61K 36/8965* (2013.01); *A61K 2035/115* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,139,779 | A | 8/1992 | Mcneff |
| 5,240,727 | A | 8/1993 | Mcneff |
| 5,279,838 | A | 1/1994 | Mcneff |
| 5,347,468 | A | 9/1994 | Rupp et al. |
| 5,363,708 | A | 11/1994 | Johnson et al. |
| 5,518,750 | A | 5/1996 | Mcneff |
| 6,440,475 | B1 | 8/2002 | Mcneff et al. |
| 6,569,843 | B1 | 5/2003 | Walker |
| 7,416,742 | B2 | 8/2008 | Mcneff et al. |
| 7,441,942 | B2 | 10/2008 | Mcneff et al. |
| 7,544,376 | B2 | 6/2009 | Mcneff et al. |
| 7,641,920 | B2 | 1/2010 | Taylor, Jr. et al. |
| 7,943,791 | B2 | 5/2011 | Mcneff |
| 8,033,047 | B2 | 10/2011 | Rasmussen et al. |
| 8,043,633 | B2 | 10/2011 | Mcneff et al. |
| 8,048,457 | B2 | 11/2011 | Larry et al. |
| 8,048,458 | B2 | 11/2011 | Mcneff et al. |
| 8,361,174 | B2 | 1/2013 | McNeff et al. |
| 8,424,451 | B2 | 4/2013 | Mcneff et al. |
| 8,663,564 | B2 | 3/2014 | Nowlan et al. |
| 8,697,893 | B2 | 4/2014 | Mcneff et al. |
| 8,887,774 | B2 | 11/2014 | Mcneff et al. |
| 9,102,877 | B2 | 8/2015 | Mcneff et al. |
| 9,107,941 | B2 | 8/2015 | Mcneff et al. |
| 9,382,491 | B2 | 7/2016 | Mcneff et al. |
| 9,388,345 | B2 | 7/2016 | Mcneff et al. |

(Continued)

FOREIGN PATENT DOCUMENTS

| | | |
|---|---|---|
| AU | 2009298189 | 11/2015 |
| CA | 2678317 | 8/2008 |
| EP | 2118116 | 11/2009 |
| MX | 330006 | 5/2015 |
| WO | 2008101007 | 8/2008 |
| WO | 2010040070 | 4/2010 |
| WO | 2010075437 | 7/2010 |
| WO | 2012142494 | 10/2012 |
| WO | 2014008355 | 1/2014 |

OTHER PUBLICATIONS

Katsunuma, Yu; et al; "Effect of Yucca shidigera Extract and Saponins on Growth of Bacteria Isolated from Animal Intestinal Tract" Animal Science, 71, 164-170, 2000 (Year: 2000).*
Chaucheyras-Durand, F; Durand, H; "Probiotics in animal nutrition and health" Beneficial Microbes, 1, 3-9, 2010 (Year: 2010).*

(Continued)

*Primary Examiner* — David W Berke-Schlessel
(74) *Attorney, Agent, or Firm* — Pauly, DeVries Smith & Deffner LLC

(57) ABSTRACT

Embodiments herein include a composition that can include one or more saponins and one or more non-pathogenic bacterial strains. In an embodiment, a method of treating an animal to reduce the bactericidal effect of protozoa is included. The method can include administering a composition comprising saponins and administering a composition comprising at least $1 \times 10^7$ colony forming units (CFU) per gram of one or more bacterial strains. The saponins can reduce a bactericidal activity of protozoa within the animal on the one or more bacterial strains. Other embodiments are also included herein.

23 Claims, No Drawings

(56) References Cited

U.S. PATENT DOCUMENTS

| | | | |
|---|---|---|---|
| 9,826,761 | B2 | 11/2017 | Mcneff et al. |
| 2004/0228207 | A1 | 11/2004 | Mcneff et al. |
| 2005/0048176 | A1 | 3/2005 | Mcneff et al. |
| 2006/0112625 | A1 | 6/2006 | Mcneff et al. |
| 2007/0071849 | A1 | 3/2007 | Mcneff |
| 2008/0194811 | A1 | 8/2008 | Mcneff |
| 2010/0005711 | A1 | 1/2010 | Mcneff |
| 2012/0190891 | A1 | 7/2012 | Mcneff et al. |
| 2012/0264955 | A1 | 10/2012 | Mcneff et al. |
| 2017/0029711 | A1 | 2/2017 | Mcneff et al. |
| 2017/0258910 | A1 | 9/2017 | Mcneff et al. |

OTHER PUBLICATIONS

Miller, KA; et al; "Orally dosing steers with Lactipro (*Megasphaera elsdenii*) decreases the quantity" Cattlemen's Day, 2013, Kansas State University, Manhattan, KS, Mar. 1, 2013, 55-58 (Year: 2013).*

Kobayashi, Yasuo; "Abatement of Methane Production from Ruminants: Trends in the Manipulation of Rumen Fermentation" Asian-Australasian Journal of Animal Sciences, 23, 410-416, 2010 (Year: 2010).*

Kurihara, Y. et al., "Relationship between bacteria and ciliate protozoa in the rumen of sheep fed on a purified diet," J. Agric. Sci., Camb. (1978), 90, 373-381 (9 pages).

Leeuw, K-J. et al., "Effect of Megasphaera elsdenii NCIMB 41125 drenching on health and performance of steers fed high and low roughage diets in the feedlot," South African Journal of Animal Science 2009, 39(4) (12 pages).

Wallace, R. J. et al., "Factors affecting the rate of breakdown of bacterial protein in rumen fluid," British Journal of Nutrition (1987), 58, 313-323 (11 pages).

* cited by examiner

SAPONIN AND BACTERIAL COMPOSITIONS AND METHODS

This application claims the benefit of U.S. Provisional Application No. 62/535,407, filed Jul. 21, 2017, the contents of which are herein incorporated by reference in their entirety.

FIELD

Embodiments herein relate to saponin and bacterial compositions and methods for using the same. More specifically, embodiments herein relate to saponin and bacterial compositions useful for mitigating the bactericidal effects of protozoa in the rumen of an animal.

BACKGROUND

Protozoa in the rumen of an animal can exhibit bactericidal effects on the populations of beneficial bacteria also present therein. Protozoa in the rumen have been shown to affect ammonia production, methane production, and rumen pH. In some cases, the bactericidal effects exhibited by protozoa can lead to acidosis within the rumen. Acidosis can occur when the pH of the rumen falls below 5.5, leading to a decrease in digestion of feed, a loss of appetite, and a decrease in animal productivity. In severe cases, acidosis in the rumen can lead to metabolic acidosis and, if left untreated, to the death of an animal.

SUMMARY

Embodiments herein relate to saponin and bacterial compositions and methods for using the same. In an embodiment, a method of treating an animal to reduce the bactericidal effect of protozoa is included. The method can include administering a composition comprising saponins and administering a composition comprising at least $1 \times 10^7$ colony forming units (CFU) per gram of one or more bacterial strains. The saponins can reduce a bactericidal activity of protozoa within the animal on the one or more bacterial strains.

In an embodiment, a composition is included herein. The composition can include one or more saponins and one or more bacterial strains. The saponins and bacterial strains can work together to prevent or reduce a bactericidal activity of protozoa present in a rumen.

In an embodiment, a method of processing animal feed is included. The method can include contacting an animal feed material with a composition, the composition including one or more saponins and one or more bacterial strains. The one or more saponins and the one or more bacterial strains can prevent or reduce a bactericidal activity of protozoa present in a rumen of an animal.

In an embodiment, a method of treating an animal to reduce the bactericidal effect of protozoa is included. The method can include administering an effective dose of a composition to the animal, the composition including one or more saponins and one or more bacterial strains. The one or more saponins and the one or more bacterial strains can work together to prevent or reduce a bactericidal activity of protozoa.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

DETAILED DESCRIPTION

Beneficial bacterial strains, also described more fully below, can assist in the digestion of feed material, including but not limited to the elimination excess gas, the prevention of acidosis in the rumen, the increase in weight gain, and the enhancement of the immune response. For that reason, dietary supplementation of beneficial bacterial strains is an approach to improving the overall health of the animal.

However, protozoa in the rumen of an animal can have a bactericidal effect on the populations of beneficial bacterial present therein. Protozoa can ingest bacteria, therefore mitigating the beneficial effects that the bacteria may otherwise have on the animal. Therefore, the efficacy of dietary supplementation of bacteria can be greatly reduced by protozoa within the animal. Exemplary protozoa found in the rumen are described more fully below.

Saponins, as described more fully below, have various beneficial dietary properties when fed to animals. Notably, saponins can kill protozoa or otherwise reduce their effects on protozoa.

Embodiments herein can include the use of saponin compositions and bacterial compositions (or saponins and bacteria integrated as a single composition) and can be used to boost the efficacy of dietary supplementation of bacteria. The saponins can prevent or reduce the effects of protozoa on the bacteria.

In some embodiments, compositions herein can be directly administered to an animal. However, in some embodiments compositions included herein can be mixed in with animal feed material. In this manner, the composition can act as a feed conditioning agent. Therefore, in an embodiment, a feed conditioning composition including saponins and at least one bacterial strain can be used to mitigate the bactericidal effects of protozoa in the rumen of animals, while increasing the efficacy of the bacterial component of the composition.

Compositions included with embodiments herein can be formulated in various ways. For example compositions herein can be formulated as a liquid, slurry, dry powder, dry granular mix, paste, pellets, block, or the like. Compositions may be administered to an animal as a pill, a bolus, or a liquid drench.

In accordance with embodiments included herein, compositions can be administered to an animal along with the animal's feed ration. For example, a composition, such as a liquid or solid composition can be mixed in with an animal's feed ration. In some embodiments, a composition, such as a liquid composition, can be mixed in with an animal's water. In some embodiments, a feed conditioning composition including at least one saponin can be administered to an animal along with the animal's feed ration, followed by an additional bolus of one or more bacterial strains at one or more time periods following the addition of the initial feed conditioning composition.

Saponins

Various compositions herein can include saponins or mixtures of saponins. Saponins are natural plant surfactants that occur in over 500 different plant species belonging to some 80 different families. They are generally recognized by their strong foaming action when placed in water, which has made them especially useful in the manufacture of foods, beverages, shampoos, wetting agents, and pharmaceuticals.

Saponins are classified as surfactants because they have both lipophilic and hydrophilic "regions." Thus, the surfactant activity of saponins is a result of both fat-soluble and water-soluble moieties in the same molecule. The lipophilic region may be a steroid, triterpene, or alkaloid, and is termed a sapogenin. The hydrophilic "region" contains one or more water-soluble carbohydrate side chains. The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration.

Saponins can play a role in reducing or eliminating ruminal protozoa, which can prevent protozoal ingestion of beneficial ruminal bacteria. Saponins (triterpenoid, steroidal, or alkaloid) have a hemolytic action that is believed to be related to their affinity for cell membrane sterols that are embedded in the lipid bi-layer, and in particular cholesterol. Saponins have been shown to form insoluble complexes with cholesterol and thereby open holes in cell membranes of ruminal protozoa to cause cell lysis. The ability of saponins to rupture cell membranes, but yet be non-toxic to mammals when ingested orally makes them a suitable protozoan eliminator for use in livestock.

In some embodiments, the saponin composition can include a saponin derived from a plant extract. Saponins suitable for use herein can be extracted from plants of the family: *Lillaecae*, genus: *Yucca*, such as *Yucca schidigera*. Yucca derived saponins generally have steroidal sapogenins, and are referred to generally as sarsaponins. Sarsaponins can include any saponin or mixture of saponins found in *Yucca schidigera*. Sarsasapogenin is the major sapogenin found in the *Yucca schidigera* plant. Saponins suitable for use herein can also be extracted from plants of the family: *Amaryllidaccae*, genus: *Agave*, which grows extensively in the southwestern United States and Mexico. Additional sources of saponins can include extracts of soybeans, fenugreek, peas, tea, yams, sugar beets, alfalfa, asparagus, aloe, vanilla, zhimu, *Sapindus saponaria*, citrus fruits (limonoid saponins) as well as from *Quillaja saponaria* bark.

The typical saponin content that naturally occurs in Yucca plants is from 0.1-2% saponins by weight. Yucca extracts can be derived by extracting yucca powder with an aqueous solution that may or may not contain some fraction of organic solvent such as methanol, ethanol, propanol, butanol, or the like.

Commercially available Yucca extracts can have total solids content usually in the range from 5-50% solids by weight. The saponin content of a typical 50 brix (50% solids by weight) yucca extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) yucca extract is usually in the range of about 5-20% saponins content by weight as measured by the butanol extract method.

In an embodiment, the composition can include at least 0.1% by weight saponins as measured by HPLC (saponin composition or integrated saponin and bacterial composition). In an embodiment, the composition can include at least 0.5% by weight saponins as measured by HPLC. In an embodiment, the composition can include at least 1.0% by weight saponins as measured by HPLC. In an embodiment, the composition can include at least 2.0% by weight saponins as measured by HPLC. In an embodiment, the composition can include at least 5.0% by weight saponins as measured by HPLC. In an embodiment, the composition can include at least 7.5% by weight saponins as measured by HPLC. In an embodiment, the composition can include at least 10.0% by weight saponins as measured by HPLC Bacterial Compositions The compositions embodied herein can include one or more beneficial bacterial strains. A healthy microbiota in an animal's gastrointestinal tract can provide numerous beneficial effects on digestion, including increased energy recovery from dietary feed materials, increased weight gain, and a decrease in the incidence of ruminal acidosis caused by abnormally high levels of acidic byproducts such as lactic acid.

The compositions herein can include one or more bacterial strains, selected from the group of non-pathogenic species including those of the genus *Megasphaera, Selenomonas, Veillonella, Mitsuokella, Lactobacillus, Bifidobacterium, Enterococcus, Bacillus, Lactococcus, Leuconostoc, Pediococcus, Sporolactobacillus, Streptococcus, Escherichia*, and *Priopionibacterium*.

In some embodiments, compositions herein can include one or more strains of lactate utilizing bacteria, which can include, but is not limited to *Megasphaera, Selenomonas, Veillonella*, and *Mitsuokella*.

In some embodiments, the species of *Megasphaera* can include, but not be limited to *Megasphaera elsdenii*. In some embodiments, the bacterium *Megasphaera elsdenii*, can be beneficial in the rumen of animals due to its ability to ferment lactic acid. The conversion of lactic acid into at least butyrate and propionate can increase the pH in the rumen and result in an increase in energy utilization by the animal. The beneficial effects of *Megasphaera elsdenii* can allow the animals to move from a growth ration to a finishing ration more quickly than without it. In some embodiments, the use of *Megasphaera elsdenii* can decrease the amount of time the animals move from a growth ration to a finishing ration by about 1, 2, 3, 4, 5, 6, 7, 8, 9, or 10 days.

In some embodiments, the species of *Selenomonas* can include, but not be limited to, *Selenomonas ruminantium*. In some embodiments, the species of *Lactobacillus* can include, but not be limited to, *Lactobacillus acidophilus, Lactobacillus casei, Lactobacillus crispatus, Lactobacillus gallinarum, Lactobacillus gasseri, Lactobacillus johnsonii, Lactobacillus paracasei, Lactobacillus plantarum, Lactobacillus reuteri*, and *Lactobacillus rhamnosus*. In some embodiments, the species of *Bifidobacterium* can include, but not be limited to *Bifidobacterium adolescentis, Bifidobacterium animalis, Bifidobacterium bifidum, Bifidobacterium breve, Bifidobacterium infantis, Bifidobacterium lactis*, and *Bifidobacterium longum*. Other suitable bacterial strains can include *Enterococcus faecalis, Enterococcus faecium, Lactococcus lactis, Leuconostoc mesenteroides, Pediococcus acidilactici, Sporolactobacillus inulinus, Streptococcus thermophilus, Bacillus cereus, Escherichia coli*, and *Propionibacterium freudenreichii*.

In some embodiments, the amount of bacteria suitable for use with embodiments herein can include an amount that is sufficient to produce the desired effects as described. In some embodiments, the amount of bacteria suitable for use in the compositions herein can include at least $1 \times 10^6$, $1 \times 10^7$, $1 \times 10^8$, or $1 \times 10^9$ colony forming units (CFU) per gram of the composition. In some embodiments, these amounts can be with regard to the sum of all strains of bacteria used and in some embodiments these amounts can be with regard to only a particular strain of bacteria used if there is more than one. Such references to CFUs herein shall, by default, refer to the sum of all strains of bacteria used unless the context dictates otherwise.

Composition Forms

The compositions herein can include saponins or mixtures of saponins and one or more bacterial strains. In some embodiments, the saponin and bacterial components can be integrated as a single composition (liquid or dry). However, in other embodiments, the saponin and bacterial components can be separated as two different compositions (liquid or dry) such that the saponins are kept separate from the bacterial strains prior to use.

In some embodiments, compositions herein (saponin, bacterial, or mixed saponin and bacterial) can include a liquid formulation. In some embodiments, the compositions can include a slurry or a paste. In some embodiments, compositions herein can specifically include an aqueous liquid formulation (saponin, bacterial, or combined saponin and bacterial composition).

In some embodiments, compositions suitable for use herein can have a water content of less than 98, 95, 90, 80, 70, 60, 50, 40, 30, 20, 10, or 5 weight percent (wt. %). In some embodiments, the compositions herein (saponin composition, bacterial composition, or combined saponin and bacterial) can have a water content in a range between any of the foregoing amounts of water provided that the upper bound is greater than the lower bound. Without being bound by theory, it is believed that reduced water content may assist in the long-term viability of a bacterial population present in the composition.

In some embodiments, liquid or dry formulations can include components to prolong the shelf-life of the composition. For example, the compositions may include oxygen scavengers, including but not limited to ascorbic acid, Vitamin E, and iron oxides. In some embodiments, the compositions herein can include water displacing additives such as glycerin, propylene glycol, and various sugars, discussed further below.

It will be appreciated that in some embodiments liquid formulations/compositions herein can be treated by sparging the compositions with an inert gas, such as nitrogen or helium, to reduce the amount of oxygen dissolved in the composition prior to sealing and packaging of the composition. In some embodiments, the composition can be sealed within a container that provides low oxygen gas permeability (e.g., 0.1 cc $O_2$/container/24 hours or 0.01 cc $O_2$/container/24 hours or less). While not intending to be bound by theory, it is believed that lower dissolved oxygen content can contribute to enhanced viability of bacterial strains used herein. In some embodiments, the amount of dissolved oxygen in a liquid composition herein (saponin composition, bacterial composition, or mixed saponin and bacterial composition) is less than 11, 10, 9, 8, 7, 6, 5, 4, 3, 2, or 1 mg/L. In some embodiments, the amount of dissolved oxygen is in a range between can of the foregoing amounts provided that the upper bound of the range is greater than the lower bound.

In some embodiments, compositions herein can be formulated as dry composition containing one or more saponins and one or more bacterial strains. In various embodiments, the dry composition can include a moisture content of less than 20, 18, 16, 14, 12, 10, 8, 6, 4, or 2 percent by weight. In some embodiments, the dry composition can include a dry powder, dry granular mix, pellets, block, or the like. In some embodiments, the one or more saponins and/or one or more bacterial strains in the dry compositions can be obtained by a spray-drying process. In other embodiments, the one or more saponins and/or one or more bacterial strains of the dry compositions can be obtained by a spray-drying process, a freeze-drying process or other drying process.

In some embodiments, the surface-area-to-volume ratio of the one or more saponins and the one or more bacterial strains in a dry composition can be tailored to provide different rates of dissolution for each component upon administration to an animal. For example, the saponin component of the dry composition can include one or more saponins present in a small particulate form, such as a fine powder, to provide a high surface-area-to-volume ratio that allows for rapid dissolution upon administration to the animal. The bacterial component of the same composition can include a large particulate form, having a lower surface-area-to-volume ratio than the saponin component, such that the bacterial component can dissolve into solution more slowly than the saponin component. Without being bound by any particular theory, it is believed that an integrated composition having a saponin component with a rapid dissolution rate and a bacterial component with a slower dissolution rate can provide immediate bactericidal activity by the saponin(s) on the protozoa present in the rumen, while not exerting an immediate effect on the bacterial component.

By way of example, the saponin component can exist as a particulate with an average size of less than about 1000, 500, 250, 120, 100, 80, 60, 40, 20, 10, or 5 μm, or in a size range between any of the foregoing. Correspondingly, the bacterial component can exist as a particulate with an average size greater than the saponin component. For example, the bacterial component can exist as a particulate with an average size of greater than 20, 40, 60, 80, 100, 120, 250, 500, 1000, 2000, or 3000 μm, or in a size range between any of the foregoing.

In some embodiments, the saponins and bacteria can be provided as separate compositions, which can either be separate liquid compositions, separate dry compositions, or one liquid and one dry composition.

It will be appreciated that the water content of the liquid formulation of the one or more saponins may be higher or lower than the water content of the liquid formulation for the separate bacterial strain component.

In the case of a non-integrated composition, the saponin composition can be administered to the animal either before or after administering the bacterial composition. For example, the saponin composition can be administered at a predetermined time before the bacterial composition. In some embodiments, the saponin composition can be administered 1 minute to 5 hours before administration of the bacterial composition. Yet in other embodiments, the saponin composition can be administered at a predetermined time after the bacterial composition. In some embodiments, the saponin composition can be administered 1 minute to 5 hours after administration of the bacterial composition. However, in other embodiments, the two compositions can be administered substantially simultaneously.

In some embodiments, the saponin composition can be administered 1 minute, 5 minutes, 10 minutes, 20 minutes, 30 minutes, 45 minutes, 1 hour, 2 hours, 3 hours, 4 hours or 5 hours before administering the bacterial composition. In some embodiments the saponin composition can be administered at a time point before administration of the bacterial component that falls within a range wherein any of the foregoing times can serve as the upper or lower bound of the range, provided that the upper bound is greater than the lower bound.

In other embodiments, the saponin composition can be administered 1 minute, 5 minutes, 10 minutes, 20 minutes, 30 minutes, 45 minutes, 1 hour, 2 hours, 3 hours, 4 hours or 5 hours after administering the bacterial composition. In some embodiments the saponin composition can be administered at a time point after administration of the bacterial composition that falls within a range wherein any of the foregoing times can serve as the upper or lower bound of the range, provided that the upper bound is greater than the lower bound.

In some embodiments herein, a kit is included. The kit can include a first composition and a second composition, the first compositions and second composition separated from one another. The first composition can be a saponin composition such as those described herein. The second composition can be a bacterial composition such as those described herein.

Rumen Protozoa

Protozoa are one of the most abundant microbes by mass found in the rumen, and they can have a deleterious bactericidal effect on the populations of beneficial bacterial present therein. Protozoa in the rumen can be ciliated or flagellated. Some of the most common genuses of protozoa found in the rumen include, but are not limited to ciliated protozoa such as *Epidinium, Entodinium, Diplodinium, Eudiplodinium, Dasytricha, Polyplastron, Isotricha, Ophryoscolex*, and *Ophryoscolex*. Compositions described herein can reduce the ruminal population of protozoa, thereby reducing the bactericidal effect of the protozoa on resident or supplemental bacterial populations.

Animal Feed Materials

In an embodiment, a method of processing animal feed including contacting an animal feed material with a composition including one or more saponins and a composition including one or more beneficial bacteria strains (or an integrated composition that includes both the saponins and the bacteria). By adding the composition(s) to the animal feed, dosing can be simplified as the composition will reach the rumen along with the feed.

It will be appreciated that animal feed materials can include many different components such as, but not limited to, alfalfa hay, alfalfa haylage, almond hulls, apple components, rolled barley, barley malt sprouts, barley silage, bermuda grass, blood meal, bluegrass, brome, canary grass, canola seed, canola meal, chocolate byproduct, dried citrus pulp, clover, sudangrass hay, dry-rolled corn, tempered-rolled corn, steam-flaked corn, ground shelled corn, cracked corn, hominy feed, corn gluten feed, corn silage, wet brewer's grain, dry brewer's grain, distillers grains (dried and wet), stillage, soybean meal, soybean seeds, soybean hulls, sunflower meal, sunflower oil, sunflower seeds, tomato products, wheat bran, rolled wheat, wheat hay, wheat middlings, wheat silage, whey, fescue, fish byproducts, hay, legumes, linseed, meat meal, meat and bone meal, rolled oats, oat hay, oat silage, orchard grass, peanut meal, potato byproduct meal, rice bran, rye, safflower, dry rolled sorghum, steam-flaked sorghum, sorghum silage, soybean hulls, whole cottonseed, cottonseed hulls, cottonseed meal, sugar beet pulp, dehydrated beet pulp, bakery waste, cottonseed meal, yellow grease, white grease, vegetable oil, palm oil, coconut oil, cottonseed oil, sunflower oil, flax seed oil, safflower oil, corn oil, soybean oil, sesame oil, canola oil, olive oil, tallow, water, hydrolyzed feather meal, cane molasses, sugar beet molasses, and the like, and combinations thereof.

In some embodiments, the animal feed material can specifically include byproducts of ethanol production. For example in some embodiments, the animal feed material can specifically include distillers dried grains, distillers wet grains, and/or stillage.

It will be appreciated that methods and compositions suitable for use herein can be used for the treatment of animals, including bovine, fowl, porcine, ovine, and equine species. By way of example, the methods and compositions suitable for use herein can be used for the treatment of cattle, chickens, turkeys, ducks, quail, geese, pigs, horses, bison, elk, and sheep. In a specific embodiment, the methods and compositions suitable for use herein can be used for the treatment of ruminants including, but not limited to, *Bos taurus*.

Method of Administration

In an embodiment, a method of treating an animal to reduce the bactericidal activity of protozoa in the rumen of an animal is included. The method can include administering an effective dose of a composition to the animal. The composition can include one or more saponins and one or more beneficial bacterial strains. The saponins and at least one or more beneficial bacterial strains can reduce the bactericidal activity of protozoa in the rumen within the animal.

In some embodiments, a method of treating an animal to reduce the bactericidal activity of protozoa in the rumen can include administering an integrated composition to the animal. In other embodiments, a method of treating an animal to reduce the bactericidal activity of protozoa in the rumen can include administering a separate composition to an animal. Administering a separate composition to an animal can include a time delay between the administration of a saponin composition and the administration of the bacterial composition, as discussed herein.

In some embodiments the method can further include selecting an animal exhibiting signs of acidosis (acute acidosis or subacute acidosis). Symptoms of acute acidosis can include little or no feed intake, little or no rumination, increased heart rate, increased breathing rate, diarrhea, and lethargy. Symptoms of subacute acidosis can include reduced feed intake, lower feed efficiency, weight loss or reduced gain, low body condition score, lameness (laminitis/founder), dehydration, liver abscesses, increased temperature, grain in manure and diarrhea. In some embodiments, the method can include selecting animals having elevated protozoal populations within their rumen fluid. Elevated protozoal populations can be assessed by sampling current protozoal populations amongst one or more animals and comparing those amounts against previous protozoal population counts in those same animals, in representative animals, in average literature values, or threshold values. In some embodiments the animal can be a ruminant. In some embodiments the animal can be *Bos taurus*.

Additional Components/Additives

It will be appreciated that compositions in accordance with embodiments herein can include various additives. By way of example, compositions can also include additives such as water, glycerin, propylene glycol, sugars, including but not limited to glucose, sucrose, fructose, dextrose, and galactose, Vitamin E (as di-alpha-tocopherol acetate), Vitamin A Propionate, Vitamin A Palmitate, Vitamin B1, Vitamin B2, Vitamin B6, Vitamin B12, Vitamin C (ascorbic acid), D-Activated Animal Sterol (source of Vitamin D3), Vitamin E, Vitamin K, Folic Acid, Niacin, Pantothenic Acid (d-calcium pantothenate), iron oxide, yeast components, dried egg solids, dried casein, dried whey, antibiotics, and natural and artificial flavorings, amongst others.

EXAMPLES

Example 1

Effect of Administration of Saponin Composition and Bacterial

Supplementation on Total Bacterial CFU Counts in Rumen Fluid

A liquid saponin composition is obtained having a saponin content of about 5.0% by weight saponins (as measured by HPLC). A separate liquid bacterial composition is obtained having a concentration of about $1 \times 10^7$ CFU per gram of *Megasphaera elsdenii*.

Cattle are selected and rumen fluid samples are taken to determine baseline bacterial CFU counts at time point 0. For a first test group of cattle, 50 ml of the saponin composition is administered at time point 0+10 minutes. For a second control group of cattle, an equal amount of water is administered at time point 0+10 minutes. At time point 0+30 minutes, 40 grams of the liquid bacterial composition is administered to both the test group of cattle and the control group of cattle. At time point 0+90 minutes, rumen fluid samples are taken from both the control group of cattle and the test group of cattle and bacterial CFU counts therein are taken. The after-treatment CFU counts are then compared with the baseline CFU counts to assess the effects of the experimental treatment. It is determined that cattle treated with saponins prior to the administration of bacterial compositions have a larger increase in CFU counts over baseline than cattle that did not receive saponins.

The embodiments described herein are not intended to be exhaustive or to limit the invention to the precise forms disclosed in the following detailed description. Rather, the embodiments are chosen and described so that others skilled in the art can appreciate and understand the principles and practices. As such, while aspects have been described with reference to various specific and preferred embodiments and techniques, it should be understood that many variations and modifications may be made while remaining within the spirit and scope herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The claims are:

1. A method of treating an animal to reduce the bactericidal effect of protozoa, the method comprising:
   administering a saponin component comprising saponins having a first dissolution rate; and
   administering a bacterial component comprising at least $1 \times 10^7$ colony forming units (CFU) per gram of one or more bacterial strains including *Megasphaera elsdenii, Selenomonas, Veillonella, Mitsuokella multicide*, the bacterial component having a second dissolution rate;
   wherein the saponins reduce a bactericidal activity of protozoa within the animal on the one or more bacterial strains; and
   wherein the first dissolution rate is greater than the second dissolution rate such that the saponin component can provide immediate bactericidal activity on protozoa present in the rumen, while not exerting an immediate effect on the bacterial component.

2. The method of claim 1, further comprising administering the composition comprising saponins at a predetermined time before administering the composition comprising one or more bacterial strains.

3. The method of claim 1, further comprising administering the composition comprising saponins at a predetermined time after administering the composition comprising one or more bacterial strains.

4. The method of claim 1, further comprising administering the composition comprising saponins and the composition comprising one or more bacterial strains simultaneously.

5. The method of claim 1, further comprising waiting for a period of time after administering the composition comprising saponins before administering the composition comprising the one or more bacterial strains.

6. The method of claim 5, wherein the period of time is in a range between 1 minute and 5 hours.

7. The method of claim 1, the composition comprising saponins comprising a plant extract.

8. The method of claim 7, the plant extract comprising an extract of agave, yucca, soybeans, citrus, fenugreek, peas, tea, yams, sugar beets, alfalfa, asparagus, aloe, vanilla, zhimu, *Sapindus saponaria*, or *Quillaja saponaria*.

9. The method of claim 7, the plant extract comprising yucca extract.

10. The method of claim 1, the saponins comprising sarsaponins.

11. The method of claim 1, wherein at least one of the composition comprising saponins and the composition comprising one or more bacterial strains is a liquid composition.

12. The method of claim 1, wherein at least one of the composition comprising saponins and the composition comprising one or more bacterial strains is a dry composition.

13. The method of claim 12, wherein both the composition comprising saponins and the composition comprising one or more bacterial strains are in a dry particulate form and the composition comprising saponins has a smaller average particle size than the composition comprising one or more bacterial strains.

14. The method of claim 1, the one or more bacterial strains further comprising at least one non-pathogenic bacterial strain selected from the genus of at least one of, *Lactobacillus, Bifidobacterium, Enterococcus, Bacillus, Lactococcus, Leuconostoc, Pediococcus, Sporolactobacillus, Streptococcus, Escherichia*, and *Priopionibacterium*.

15. The method of claim 1, the one or more bacterial strains comprising *Megasphaera elsdenii*.

16. The method of claim 1, wherein the composition comprising saponins and the composition comprising one or more bacterial strains are part of an integrated composition.

17. The method of claim 1, wherein the composition comprising saponins and the composition comprising one or more bacterial strains are separate compositions.

18. The method of claim 1, further comprising selecting an animal exhibiting signs of acidosis.

19. The method of claim 1, further comprising selecting an animal exhibiting signs of acute acidosis.

20. The method of claim 1, further comprising selecting an animal exhibiting signs of subacute acidosis.

21. The method of claim 1, further comprising selecting animals having elevated protozoal populations within their rumen fluid.

22. A composition comprising:
- a saponin component comprising one or more saponins, the saponin component having a first dissolution rate; and
- a bacterial component comprising at least $1 \times 10^7$ colony forming units (CFU) per gram of one or more bacterial strains including *Megasphaera elsdenii, Selenomonas, Veillonella, Mitsuokella multicida*, the bacterial component having a second dissolution rate;

wherein the first dissolution rate is greater than the second dissolution rate such that the saponin component can provide immediate bactericidal activity on protozoa present in the rumen, while not exerting an immediate effect on the bacterial component.

23. A method of processing animal feed comprising:
- contacting an animal feed material with a composition, the composition comprising:
- a saponin component comprising one or more saponins, the saponin component having a first dissolution rate; and
- a bacterial component comprising one or more bacterial strains, the bacterial component having a second dissolution rate;

wherein the first dissolution rate is greater than the second dissolution rate such that the saponin component can provide immediate bactericidal activity on protozoa present in the rumen, while not exerting an immediate effect on the bacterial component.

* * * * *